United States Patent [19]

Blum et al.

[11] Patent Number: 5,300,682
[45] Date of Patent: Apr. 5, 1994

[54] CATALYTIC OXIDATION OF ETHANE TO ACETIC ACID

[75] Inventors: Patricia R. Blum, Macedonia; Marc A. Pepera, Northfield, both of Ohio

[73] Assignee: The Standard Oil Co., Cleveland, Ohio

[21] Appl. No.: 878,116

[22] Filed: Apr. 29, 1992

Related U.S. Application Data

[63] Continuation-in-part of Ser. No. 712,293, Jun. 10, 1991.

[51] Int. Cl.$^5$ ............... C07C 27/10; C07C 51/16; C07C 53/00
[52] U.S. Cl. ................ 562/512.2; 562/549; 568/910
[58] Field of Search ............ 562/512.2, 549; 568/910

[56] References Cited

U.S. PATENT DOCUMENTS 2,020,671 11/1935 Dreyfus .................. 260/116
4,410,752 10/1983 Blum et al. ............... 585/658

OTHER PUBLICATIONS

Thorsteinson et al., Journal of Catalysis, vol. 52, pp. 116-132 (1978).

*Primary Examiner*—José G. Dees
*Assistant Examiner*—Porfirio Nazario
*Attorney, Agent, or Firm*—Charles S. Lynch; Michael F. Esposito; David J. Untener

[57] ABSTRACT

Disclosed is a process for making acetic acid which comprises oxidizing ethane with molecular oxygen in a reaction zone at a pressure of at least 100 psig while the reactants are in contact with a solid catalyst having the elements and relative atomic proportions indicated by the empirical formula:

$$VP_aM_bO_x$$

where M is one or more optional element selected from Co, Cu, Re, Fe, Ni, Nb, Cr, W, U, Ta, Ti, Zr, Zn, Hf, Mn, Pt, Pd, Sn, Sb, Bi, Ce, As, Ag, and Au, wherein
  a is 0.5 to 3,
  b is 0 to 1, and
  x is a number determined by the valence requirements of the other elements in the catalyst, and
wherein said catalyst contains crystalline vanadyl pyrophosphate.

8 Claims, No Drawings

CATALYTIC OXIDATION OF ETHANE TO ACETIC ACID

This application is a continuation-in-part of application Ser. No. 712,293, filed Jun. 10, 1991.

The present invention relates to the catalytic oxidation of ethane to acetic acid.

U.S. Pat. No. 4,410,752 discloses the reaction of ethane and oxygen to make ethylene over a solid unsupported or supported catalyst having the formula $VP_aM_bO_x$ where M is an optional promoter element. At the time of filing the application which eventually matured of said patent, it was believed that such catalyst was ineffective to convert ethane to acetic acid in the presence of oxygen.

It is an object of the present invention to provide a process for oxidizing ethane to obtain acetic acid as a desired product.

We have now discovered that this objective can be realized with a V-P-O catalyst if certain reaction conditions are observed.

According to the invention there is provided a process for making acetic acid which comprises oxidizing ethane with molecular oxygen in a reaction zone at a pressure of at least 100 psig while the reactants are in contact with a solid catalyst having the elements and relative atomic proportions indicated by the empirical formula:

$$VP_aM_bO_x$$

where M is one or more optional element selected from Co, Cu, Re, Fe, Ni, Nb, Cr, W, U, Ta, Ti, Zr, Zn, Hf, Mn, Pt, Pd, Sn, Sb, Bi, Ce, As, Ag and Au, wherein a is 0.5 to 3 (usually 0.85 to 2), b is 0 to 1 (usually 0–0.4), and x is a number determined by the valence requirements of the other elements in the catalyst, and wherein said catalyst contains crystalline vanadyl pyrophosphate, $(VO)_2P_2O_7$.

It is also preferred that the mol ratio of ethane to molecular oxygen fed to said reaction zone be at least 2, usually at least 3, since the selectivity of conversion of ethane to acetic acid is enhanced when compared to lower ratios. The maximum mol ratio of ethane to $O_2$ usually does not exceed 15, although higher ratios can be used.

Usual reaction pressure are at least 150 psig. Pressures as high as 500 psig and higher can be used if desired.

It should also be mentioned that said catalyst need contain no Mo at all, but if present, it is never present in an amount exceeding 0.5 atoms per atom of V in the catalyst.

The reaction is effected at temperatures in the range from 250° to 450° C., usually 300° to 400° C.

The present process co-produces ethylene with the acetic acid. The acetic acid can be recovered from the gaseous ethylene and unreacted ethane. The ethane can be separated in a known manner from the ethylene and recycled to the present reaction. The ethylene can be recovered as valuable product or oxidized with molecular oxygen to more acetic acid over a catalyst that efficiently converts ethylene to acetic acid.

It is also possible to recover the ethane-ethylene mixture from the effluent of the present reaction zone and to carry out the mentioned oxidation of ethylene to acetic acid without previously removing the ethane. After recovering the acetic acid from the product, the ethane can be recycled as feed to the present reaction to make acetic acid.

The catalyst composition used in the claimed process can be unsupported or supported on such supports as alumina, silica, silicaalumina, etc.

Regarding the use of promoter metals, we have found that while the vanadium, phosphorus, oxygen catalyst performed well for the present oxidation reaction the addition of one or more promoter metals does not weaken or destroy the activity of the catalyst by changing its crystalline structure, but rather the presence of the crystalline $(VO)_2P_2O_7$ is maintained. The presence of the optional promoter element(s) often allows for an easing of reaction conditions such as permitting lower reaction temperatures, shorter contact times and the like.

The ethane is fed to the reactor together with molecular oxygen as pure oxygen gas, or as air, or as oxygen in an inert gas such as nitrogen. In addition to $N_2$, or instead of $N_2$, other essentially inert diluents such as helium, methane, $CO_2$ and argon can be introduced to the reaction zone.

The following examples are exemplary and should not be taken as in any way limiting the invention claimed herein.

The catalyst examples describe the making of the catalysts used in the examples of the process. All of the catalysts contain crystalline $(VO)_2P_2O_7$ unless otherwise noted.

CATALYST EXAMPLE I

A 40 g sample of $(VO)_2P_2O_7$ (vanadyl pyrophosphate) was heated at approximately 420° C. under an air/butane atmosphere, ballmilled, and slurried in one hundred ml of distilled water. The slurry was heated to near the boiling point (75°–95° C.) and the water was evaporated. The solid was dried overnight at 120° C. The solid was then ground and screened to 10/40 mesh sized particles. The catalyst empirical formula was $(VO)_2P_2O_7$.

CATALYST EXAMPLE II

This catalyst was prepared the same as Example I, except that it was ground and screened to 10/30 mesh size particles and then calcined for 3 hrs in air at 350° C. Its empirical formula was $(VO)_2P_2O_7$.

CATALYST EXAMPLE III

This catalyst was prepared by the same method as Example I except that ammonium perrhenate was added to the catalyst slurry prior to boiling it to dryness (30.78 g of $(VO)_2P_2O_7$, 8.05 g of $NH_4ReO_4$, one hundred ml of distilled water). The solid was dried overnight at 120° C. The solid was then ground and screened to 10/30 mesh sized particles and calcined for 3 hrs in air at 350° C. Elemental analysis of the final catalyst gave the following empirical formula: $V_{1.0}P_{1.0}Re_{0.016}O_x$.

CATALYST EXAMPLE IV 34.38 g of $(VO)(HPO_4)\cdot\frac{1}{2}H_2O$ was slurried in 100 ml of distilled water. To this was added a solution containing 0.8 g of ammonium perrhenate. The resulting slurry was heated to near the boiling point (75°–95° C.) and the water was evaporated. The solid was dried overnight at 120° C. The solid was then ground and screened to 10/30 mesh sized particles and calcined for 3 hrs in air at 350° C. It was then heated under an atmosphere parts air to 1 part butane at 400° C. for 24 hours. Elemental analysis at this time gave a formulation of $V_{1.0}P_{1.0}Re_{0.03}O_x$.

CATALYST EXAMPLE V

Step 1: About 91 g $V_2O_5$ and about 112 g of a mixed phosphoric acid source containing about 49% orthophosphoric acid, 42% pyrophosphoric acid, 8% triphosphoric acid, and 1% higher polyphosphoric acids was added to about 1.5 liters isobutanol with stirring, and the resulting slurry refluxed for about 16 hours. The slurry was cooled and the catalyst precursor was recovered by filtration. This solid was dried in air at about 150° C.

Step 2: About 34.4 g (0.2 atoms of vanadium) of the above solid was finely ground and suspended in 100 ml of methanol. To this was added 0.8 g of $NH_4ReO_4$ and the mixture was heated gently ($\sim 60°$–75° C.) for three hours. The mixture was then boiled down to a thick paste and dried overnight at 110° C. The solid was ground and screened to pass through 10 mesh and be retained on 30 mesh screens. This solid was calcined for 3 hrs at 350° C. The solid was then heated for 24 hrs at 400° C. under an atmosphere of 1.8% n-butane in air. The empirical formula of the solid after this treatment was found to be $V_{1.0}P_{1.0}Re_{0.005}$. The predominate phase present in this material was identified by its X-ray diffraction pattern to be well crystallized $(VO)_2P_2O_7$.

CATALYST EXAMPLE VI

A 122.7 g sample of $(VO)_2P_2O_7$, which had been heated at approximately 420° C. under an air/butane atmosphere was ballmilled then slurried in 200 ml of distilled water. The slurry was heated to near the boiling point (75°–95° C.) and the water was evaporated. The solid was then dried at about 108° C. overnight. The final solid was ground and screened. The fraction which passed through a 10 mesh screen but was retained on a 40 mesh screen was used in the reactor tests. The catalyst empirical formula was $(VO)_2P_2O_7$.

The following specific examples were effected by passing ethane through a tubular stainless steel tubular microreactor containing the volume of catalyst shown in the Table. The reactor tube was contained in a suitcase furnace heated to the temperature shown as the "bath" temperature in the table. The table also shows the peak temperature reached in each example, as well as the reactor pressure and the ratios of the feed gases, the total feed rate in cc/min. at room temperature and pressure, as well as the WWH. Results are also shown in the table. The examples designated by letters are comparative examples.

As will be evident to those skilled in the art, various modifications of this invention can be made or followed in the light of the foregoing disclosure and discussion without departing from the spirit and scope of the disclosure or from the scope of the claims.

TABLE

| CATALYST | | | Total FEED cc/min. | Mol Ratios of Feed Ethane/$O_2$/$N_2$ | WWH[1] | Press. PSIG | TEMP., °C. | | Percent Conv. $C_2H_6$ | % Selectivity | |
|---|---|---|---|---|---|---|---|---|---|---|---|
| Ex. No. | No. | cc. | | | | | Bath | Catalyst Bed | | $C_2H_4$ | HOAc |
| 1 | II | 15 | 221 | 121/2.4/75 | 0.40 | 200 | 300 | 306 | 3.4 | 54.0 | 13.4 |
| 2 | II | 15 | 221 | " | 0.40 | 200 | 325 | 333 | 5.7 | 48.0 | 14.8 |
| 3 | I | 20 | 307 | 122/22/189 | 0.31 | 400 | 325 | 336 | 6.7 | 49.3 | 10.7 |
| 4 | I | 20 | 307 | " | 0.31 | 300 | 325 | 334 | 5.9 | 61.7 | 8.6 |
| 5 | I | 20 | 306 | 122/22/188 | 0.31 | 200 | 350 | 360 | 9.2 | 63.4 | 7.5 |
| A | I | 20 | 306 | " | 0.31 | 0 | 350 | 356 | 2.8 | 93.9 | 1.0 |
| 6 | I | 20 | 302 | 4.3/23.4/305 | 0.01 | 300 | 325 | 332 | 35.3 | 35.1 | 4.1 |
| 7 | I | 20 | 302 | " | 0.01 | 200 | 350 | 358 | 52.7 | 26.8 | 3.1 |
| B | III | 15 | 222 | 122/24/75 | 0.57 | 15 | 325 | 332 | 3.8 | 72.5 | 0.0 |
| 8 | III | 15 | 222 | " | 0.57 | 200 | 325 | 335 | 4.4 | 8.2 | 27.1 |
| 9 | IV | 19 | 305 | 10/1.8/15.6 | 0.43 | 300 | 338 | 349 | 5.4 | 46.5 | 7.2 |
| 10 | IV | 19 | 305 | " | 0.43 | 200 | 350 | 360 | 5.6 | 65.5 | 4.3 |
| 11 | IV | 7.5 | 268 | 5/1/5 | 1.17 | 300 | 350 | 364 | 4.8 | 49.9 | 8.8 |
| 12 | V | 8.5 | 271 | " | 1.45 | 300 | 350 | 361 | 5.3 | 55.1 | 5.9 |
| C | V | 8.5 | 260 | " | 1.44 | 10 | 325 | 328 | 0.5 | 95.8 | 0.0 |
| 13 | VI | 20 | 299 | 108/21/170 | 0.30 | 200 | 350 | 362 | 9.0 | 60.2 | 7.5 |
| 14 | VI | 20 | 299 | 108/21/170 | 0.30 | 100 | 360 | 370 | 9.0 | 74.3 | 4.8 |
| D | VI | 20 | 297 | 108/20/168 | 0.29 | 0 | 400 | 408 | 8.0 | 86.8 | 0.7 |

[1] Weight of ethane fed per hour per unit weight of catalyst.

We claim:

1. A process for making acetic acid which comprises oxidizing ethane with molecular oxygen in a reaction zone at a pressure of at least 100 psig while the reactants are in contact with a solid catalyst having the elements and relative atomic proportions indicated by the empirical formula:

$$VP_aM_bO_x$$

where M is one or more optional element selected from Co, Cu, Re, Fe, Ni, Nb, Cr, W, U, Ta, Ti, Zr, Zn, Hf Mn, Pt, Pd, Sn, Sb, Bi, Ce, As, Ag and Au, wherein
a is 0.5 to 3, and b is 0 to 1, and
x is a number determined by the valence requirements of the other elements in the catalyst, and wherein said catalyst contains crystalline vanadyl pyrophosphate, $(VO)_2P_2O_7$.

2. A process according to claim 1 wherein the mol ratio of ethane to molecular oxygen fed to said reaction zone is at least 2.

3. A process according to claim 1 wherein the mol ratio of ethane to molecular oxygen fed to said reaction zone is at least 3.

4. A process according to claim 1 wherein the pressure is at least 150 psig.

5. A process according to claim 2 wherein the pressure is at least 150 psig.

6. A process according to claim 3 wherein the pressure is at least 150 psig.

7. A process according to claim 1 wherein a is 0.85 to 2.

8. A process according to claim 2 wherein b is 0 to 0.4.

* * * * *